United States Patent [19]
Mather et al.

[11] Patent Number: 5,122,469
[45] Date of Patent: Jun. 16, 1992

[54] METHOD FOR CULTURING CHINESE HAMSTER OVARY CELLS TO IMPROVE PRODUCTION OF RECOMBINANT PROTEINS

[75] Inventors: Jennie P. Mather, Millbrae; Mary C. Tsao, Burlingame, both of Calif.

[73] Assignee: Genentech, Inc., South San Francisco, Calif.

[21] Appl. No.: 592,107

[22] Filed: Oct. 3, 1990

[51] Int. Cl.$^5$ ............................ C12N 5/00; C12N 5/02
[52] U.S. Cl. ............................ 435/240.2; 435/240.1; 435/240.3; 435/240.31
[58] Field of Search ............... 435/240.1, 240.2, 240.3, 435/240.31

[56] References Cited

U.S. PATENT DOCUMENTS

| Re. 30,985 | 6/1982 | Cartaya | 435/240 |
|---|---|---|---|
| 4,049,494 | 8/1977 | Tomei | 424/89 |
| 4,205,126 | 5/1980 | Cartaya | 435/2 |
| 4,282,326 | 8/1981 | Moldenhauer | 435/240 |
| 4,499,064 | 2/1985 | Shire | 435/240 |
| 4,533,637 | 8/1985 | Yamane | 435/240 |
| 4,560,655 | 12/1985 | Baker | 435/241 |
| 4,657,866 | 4/1987 | Kumar | 435/240 |
| 4,673,649 | 6/1987 | Boyce | 435/240 |
| 4,767,704 | 8/1988 | Clevland | 435/68 |
| 4,786,599 | 11/1988 | Cheesebeuf | 435/240.31 |
| 4,798,796 | 1/1989 | Wilson | 435/212 |
| 4,816,401 | 3/1989 | Taupier | 435/240 |
| 4,927,762 | 5/1990 | Darfler | 435/240.31 |

FOREIGN PATENT DOCUMENTS

| 0360205 | 3/1990 | European Pat. Off. . |
|---|---|---|
| 8700195 | 1/1987 | PCT Int'l Appl. . |
| 8800967 | 2/1988 | PCT Int'l Appl. . |
| 9003430 | 4/1990 | PCT Int'l Appl. . |

OTHER PUBLICATIONS

Velez et al., J. of Immunological Methods, 86 (1), 1986, pp. 45-52 (Biosis Abstract only).
Murhammer et al., Biotechnol. Prog., 6, (5), 1990 pp. 391-397 (Biosis Abstract only).
Cleveland et al., 4,767,704, filed Oct. 7, 1983 (abstract only), Chem. Abstract p. 2485 (1988).
Ham et al., *Meth. Enzymol.*, 58:44-93 (1979).
Mather, *Meth. Enzymol.*, 185:567-577 (1990).
McKeehan et al., *The Growth Requirements of Vertebrate Cells In Vitro*, (Cambridge University Press, NY [1981] pp. 223-243.
Ahmed et al., *J. Neurosci.*, 3:2448-2462 (1983).
Barnes et al., *Anal. Biochem.*, 102:255-270 (1980).
Bodecker et al., *Devel. Biol. Stand.*, 60:93-100 (1985).
Bottenstein, *Meth. Enzymol.*, 58:94-109 (1979).
Ham, *Methods for Serum-Free Culture of Epithelial and Fibroblastic Cells*, (Alan R. Liss, Inc., NY [1984] pp. 249-264.
Ham et al., *In Vitro Cell Devel. Biol.*, 24:833-844 (1988).
Ham et al., *Cellular & Molec. Biol. of Muscle Devel.*, (Alan R. Liss, NY [1989]) pp. 905-914.
Hammond et al., *Proc. Natl. Acad. Sci. USA*, 81:5435-5439 (1984).
Hussa et al., *Oncology*, 43:54-59 (1986).
Kan et al., *J. Cell. Physiol.*, 111:155-162 (1982).
Kane et al., *J. Exp. Zool.*, 247:183-187 (1988).
Kumar, *Neurochem. Res.*, 8:847-852 (1983).
Loo et al., *J. Cell. Physiol.*, 139:484-491 (1989).
Michler-Stuke et al., *J. Neurosci. Res.*, 7:215-228 (1982).
Sato et al., *Exp. Cell. Res.*, 138:127-134 (1982).
Serrero et al., *Hormones and Cell Culture*, pp. 523-530 (Cold Spring Harbor Laboratory Press, NY [1978]).

(List continued on next page.)

Primary Examiner—Douglas W. Robinson
Assistant Examiner—Susan M. Weber

[57] ABSTRACT

A method for culturing mammalian cells to improve production of recombinant proteins is provided. The culture media contain high levels of selected amino acids and may be supplemented with various growth factors and trace elements. In addition, the media are optionally serum-free. The media are preferably used for suspension culturing of Chinese hamster ovary cells at high densities.

5 Claims, 2 Drawing Sheets

OTHER PUBLICATIONS

Van Der Haegen et al., *In Vitro Cell. Devel. Biol.*, 25:158–162 (1989).

Waymouth, *The Growth Requirements of Vertebrate Cells In Vitro*, pp. 33–47 (Cambridge University Press, NY [1981]).

Wagner et al., *Cytotechnol.*, 1:145–150 (1988).

Ham, *Methods for Preparation of Media Supplements and Substrata for Serum Free Animal Culture*, pp. 3–21 (Alan R. Liss, Inc. NY [1984]).

Ham, *Cold Spring Harbor Conference on Cell Proliferation*, vol. 9, pp. 39–60 (Cold Spring Harbor Lab. Press NY [1984]).

Carver et al., *In Vitro*, 19:699–706 (1983).

Gasser et al., *In Vitro Cell. Devel. Biol.*, 21:588–592 (1985).

Hamilton et al., *In Vitro*, 13:537–547 (1977).

Mendiaz et al., *In Vitro Cell. Devel. Biol.*, 22:66–74 (1986).

METHOD FOR CULTURING CHINESE HAMSTER OVARY CELLS TO IMPROVE PRODUCTION OF RECOMBINANT PROTEINS

BACKGROUND OF THE INVENTION

I. Field of the Invention

This invention relates to a culture medium for propagating various mammalian cell lines. In particular, it is directed to a chemically defined culture medium containing elevated levels of certain amino acids. The medium supports the growth of mammalian cells at high densities as monolayers or in suspension, and the medium may be used for small-scale or for large-scale propagation of mammalian cells.

II. Description of Background and Related Art

A wide variety of cell types have been isolated from mammalian tissues and organs. Most of these cells can be propagated in a liquid medium that contains all of the nutrients and growth factors required to support the growth of the cells. Different cell types often have varied nutritional and growth factor requirements, and thus many distinct media have been developed to meet the differing needs of each cell type. Some of the original media developed for culturing mammalian cells require the addition of serum extracted from blood. Sera commonly used as additives include FBS (fetal bovine serum) and FCS (fetal calf serum). The use of this serum has been problematic primarily because of its prohibitive cost. It is usually the most expensive ingredient in the culture medium. In addition, serum frequently contains a large number of uncharacterized ingredients, and the quality and quantity of these ingredients can vary between lots and between vendors. Thus, serum may introduce particular components into the culture medium that may inhibit or otherwise affect the growth of cells that are cultured in the medium. To overcome these problems, there has been a trend towards developing serum-free media for propagating mammalian cell cultures. One common method for achieving this goal has been to use publicly available media that historically have been supplemented with serum, and to supplement instead with various components including vitamins, minerals, trace elements, hormones, serum albumin, lipids/fatty acids, and/or hormones and other growth factors. A review of many of the media developed for culturing eukaryotic cells is presented in Ham and McKeehan (*Meth. Enz.*, 58:44 [1979]; see also Bottenstein et al., *Meth. Enz.*, 58:94 [1979]).

Several cell lines originating from Chinese hamster have been used successfully to produce recombinant proteins. A variety of cell culture media have been specifically developed for culturing one or more of these cell lines.

Hamilton and Ham (*In Vitro*, 13:537 [1977]) developed a protein-free synthetic medium for clonal growth of Chinese hamster ovary cell lines. This medium is based on commercially available F12 medium (Sigma Chemical Company, St. Louis, MO) but contains increased amounts of calcium chloride and glutamine, is supplemented with 19 organic ions and selenium, and has a decreased level of cysteine.

Carver et al. (*In Vitro*, 19:699 [1983]) prepared several Chinese hamster ovary cell line culture media. The media are based on either F12 or Eagle's minimum essential medium (MEM), and are modified by the addition of various supplements, and/or altering the concentration of serum added to each medium.

Gasser et al. (*In Vitro Cell. Devel. Biol.*, 88 21:588 [1985]) developed a serum-free medium for culturing Chinese hamster ovary cell lines. The medium is a 1:1 mixture of F12:MEM supplemented with transferrin, insulin, and selenium.

Mendiaz et al. (*In vitro Cell. Devel. Biol.*, 22:66 [1986]) disclosed a defined medium for culturing CHO cells. The medium is F12 medium supplemented with various components including seven amino acids.

While some of the above cited work has resulted in production of cell culture media for Chinese hamster cell lines that are chemically defined and serum-free, the media may be expensive and/or laborious to prepare. In addition, these media have not been optimized for high density growth of cell lines that have been genetically engineered to produce and secrete proteins and other biological compounds of commercial interest. Thus, there is a continuing need in the art for developing cell culture media that are simple to prepare, economical, and that provide all of the necessary nutrients and growth factors, at suitable concentrations, to optimize the growth of the cells.

Accordingly, it is an object of this invention to prepare culture media that support the growth of various mammalian cell lines. Another object of this invention is to provide culture media that are preferably serum-free and that may be used in either small-scale cultures or preferably in large-scale commercial production of mammalian cells. A further object of this invention is to provide media that are suitable for high density culturing of mammalian cells. Yet another object of this invention is to provide a cell culture medium that serves to increase the yield of biological products produced by the cells cultured in the media. A further object of this invention is to provide culture media that are completely chemically defined. Another object of this invention is to provide culture media that are economical to produce. One other object of this invention is to provide a method of culturing mammalian cells in a suitable medium for growth and production of biological compounds of interest.

These and other objects will be apparent to one of ordinary skill in the art.

SUMMARY OF THE INVENTION

In accordance with the objects of this invention, a method for culturing mammalian cells is provided in which the cells are cultured in a medium containing the following components: asparagine at a concentration of from about 300 mg/l to about 750 mg/l, aspartic acid at a concentration of from about 300 mg/l to about 650 mg/l, glycine at a concentration of from about 300 mg/l to about 500 mg/l, isoleucine at a concentration of from about 300 mg/l to about 500 mg/l, leucine at a concentration of from about 400 mg/l to about 700 mg/l, lysine at a concentration of from about 1000 mg/l to about 2250 mg/l, methionine at a concentration of from about 80 mg/l to about 350 mg/l, serine at a concentration of from about 500 mg/l to about 750 mg/l, threonine at a concentration of from about 500 mg/l to about 950 mg/l, tryptophan at a concentration of from about 75 mg/l to about 230 mg/l, tyrosine at a concentration of from about 175 mg/l to about 400 mg/l, and valine at a concentration of from about 250 mg/l to about 640 mg/l, and folic acid at a concentration of from about 13.5 mg/l to about 35 mg/l.

In one particularly preferred embodiment, the cell culture medium does not require serum.

In another particularly preferred embodiment, the cell culture medium is used for culturing Chinese hamster ovary (CHO) cells.

In a further particularly preferred embodiment, CHO cells are cultured in suspension at a density of at least 100,000 cells per milliliter.

In other preferred embodiments, the cell culture medium may be supplemented with insulin, transferrin, linoleic acid, and/or trace elements.

DETAILED DESCRIPTION OF THE INVENTION

I. DEFINITIONS

The terms "cell culture medium", "culture medium", and "nutrient mixture" refer to a nutrient solution used for growing mammalian cells that typically provides at least one component from one or more of the following categories:

1) an energy source, usually in the form of a carbohydrate such as glucose;
2) all essential amino acids, and usually the basic set of twenty amino acids plus cystine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The nutrient mixture may optionally be supplemented with one or more component from any of the following categories:

1) hormones and other growth factors as, for example, insulin, transferrin, and epidermal growth factor;
2) salts and buffers as, for example, calcium, magnesium, and phosphate; and
3) nucleosides such as, for example, adenosine and thymidine.

The term "mammalian cells" refers to cell lines derived from mammals that are capable of growth and survival when placed in either monolayer culture or in suspension culture in a medium containing appropriate nutrients and growth factors. The necessary nutrients and growth factors for a particular cell line are readily determined empirically without undue experimentation, as described for example in *Mammalian Cell Culture* (Mather, J. P. ed., Plenum Press, N. Y. [1984]), and by Barnes and Sato (*Cell*, 22:649 [1980]). Typically, the cells are capable of expressing and secreting large quantities of a particular protein of interest (typically a recombinant protein) into the culture medium, and are cultured for this purpose. However, the cells may be cultured for a variety of other purposes as well, and the scope of this invention is not limited to culturing the cells only for production of recombinant proteins. Examples of suitable mammalian cell lines, capable of growth in the media of this invention, include monkey kidney CVI line transformed by SV40 (COS-7, ATCC CRL 1651); human embryonic kidney line 293S (Graham et al., *J. Gen. Virolo.*, 36:59 [1977]); baby hamster kidney cells (BHK, ATCC CCL 10); mouse sertoli cells (TM4, Mather, *Biol. Reprod.*, 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 5I); rat hepatoma cells (HTC, MI.54, Baumann et al., *J. Cell Biol.*, 85:1 [1980]); and TR-1 cells (Mather et al., *Annals N.Y. Acad. Sci.*, 383:44 [1982]) and hybridoma cell lines. Chinese hamster ovary cells (Urlab and Chasin, *Proc. Natl. Acad. Sci. USA*, 77:4216 [1980]) are a preferred cell line for practicing this invention.

The terms "amino acids" and "amino acid" refer to all naturally occurring alpha amino acids in both their D and L stereoisomeric forms, and their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine.

The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

II. DESCRIPTION OF CULTURE MEDIA

Development of the culture media of this invention is based in part on the discovery that mammalian cell lines can show enhanced growth in suspension culture when the culture medium contains very high levels of particular amino acids. Thus, in its broadest form, this invention encompasses a mammalian cell culture medium with elevated levels of certain amino acids. These amino acids, suitable concentration ranges, and preferred concentration ranges, in milligrams per liter (mg/l), are listed in Table 1 below.

TABLE 1

| Amino Acid | Suitable Concentration (mg/l) | Preferred Concentration (mg/l) |
|---|---|---|
| Asn | 300–750 | 300–625 |
| Asp | 300–650 | 300–500 |

TABLE 1-continued

| Amino Acid | Suitable Concentration (mg/l) | Preferred Concentration (mg/l) |
|---|---|---|
| Gly | 300–500 | 300–400 |
| Ile | 300–500 | 300–400 |
| Leu | 400–700 | 400–550 |
| Lys | 1000–2250 | 1000–2150 |
| Met | 80–350 | 80–200 |
| Ser | 500–750 | 500–600 |
| Thr | 500–950 | 650–800 |
| Trp | 75–230 | 75–125 |
| Tyr | 175–400 | 175–250 |
| Val | 250–640 | 250–490 |

The most preferred concentration for each of the amino acids is as follows: Asn at 589 mg/l; Asp at 465 mg/l; Gly at 329 mg/l; Ile at 331 mg/l.; Leu at 491 mg/l; Lys at 2007 mg/l; Met at 153 mg/l; Ser at 557 mg/l; Thr at 749 mg/l; Trp at 75 mg/l; Tyr at 194 mg/l; and Val at 439 mg/l.

For convenience, each amino acid can be weighed out in a predetermined amount; the amino acids can then be combined together and stored as the amino acid supplement mixture.

The medium used to practice this invention may be any mammalian cell culture medium, provided that the naturally occurring twenty amino acids and cystine are present at about the molar ratios listed in Table 2.

TABLE 2

| Amino Acid | Molar Ratio to Tryptophan |
|---|---|
| Alanine | 4.72 |
| Arginine, monohydrochloride | 49.99 |
| Asparagine, monohydrate | 4.72 |
| Aspartic Acid | 4.72 |
| Cysteine, monohydrochloride, monohydrate | 9.45 |
| Cystine, dihydrochloride | 1.35 |
| Glutamic Acid | 4.71 |
| Glutamine | 148.35 |
| Glycine | 7.42 |
| Histidine, monohydrochloride, monohydrate | 6.08 |
| Isoleucine | 6.82 |
| Leucine | 10.12 |
| Lysine, monohydrochloride | 14.83 |
| Methionine | 2.77 |
| Phenylalanine | 4.11 |
| Proline | 14.18 |
| Serine | 7.42 |
| Threonine | 10.10 |
| Tryptophan | 1.00 |
| Tyrosine, disodium salt, dihydrate | 4.06 |
| Valine | 10.13 |

One appropriate cell culture medium that may be supplemented with amino acids at elevated levels is the medium PS-04. The components of this medium are listed in Table 3 below.

TABLE 3

| Component | Concentration (mg/l) |
|---|---|
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Hypoxanthine | 16.695 |
| Linoleic acid | 0.294 |

TABLE 3-continued

| Component | Concentration (mg/l) |
|---|---|
| Lipoic acid | 0.735 |
| Putrescine, dihydrochloride | 0.5635 |
| Sodium pyruvate | 385.0 |
| Thymidine | 2.555 |
| Alanine | 31.15 |
| Arginine, monohydrochloride | 780.5 |
| Asparagine, monohydrate | 52.53 |
| Aspartic acid | 46.55 |
| Cysteine, monohydrochloride, monohydrate | 122.92 |
| Cystine, dihydrochloride | 31.285 |
| Glutamic acid | 51.45 |
| Glutamine | 1606.0 |
| Glycine | 41.25 |
| Histidine, monohydrochloride, monohydrate | 94.36 |
| Isoleucine | 66.29 |
| Leucine | 98.35 |
| Lysine, monohydrochloride | 200.75 |
| Methionine | 30.68 |
| Phenylalanine | 50.36 |
| Proline | 120.75 |
| Serine | 57.75 |
| Threonine | 89.15 |
| Tryptophan | 15.14 |
| Tyrosine, disodium salt, dihydrate | 79.125 |
| Valine | 87.95 |
| Biotin | 0.0256 |
| D-Calcium pantothenate | 3.68 |
| Choline chloride | 50.86 |
| Cyanocobalamin | 4.76 |
| Folic acid | 6.55 |
| i-Inositol | 66.60 |
| Nicotinamide | 2.1295 |
| Pyridoxal, monohydrochloride | 2.000 |
| Pyridoxine, monohydrochloride | 0.217 |
| Riboflavin | 0.3330 |
| Thiamine, monohydrochloride | 3.190 |
| Glucose | 4300.0 |
| Sodium bicarbonate | 1220.0 |
| Sodium chloride (to 350 mOsm) | 7360.0 |
| Pluronic F-68 Prill | 1000.0 |
| Gentamycin sulfate | 100.0 |

For convenience, the solid ingredients of the medium may be combined together with the amino acids, and this mixture may be stored as a single unit.

One preferred medium of this invention that contains the selected amino acids at the elevated levels is the medium called 'Super'. The ingredients and the preferred concentrations are listed below in Table 4.

TABLE 4

| Component | Concentration (mg/l) |
|---|---|
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Hypoxanthine | 16.695 |
| Linoleic acid | 0.294 |
| Lipoic acid | 0.735 |
| Putrescine, dihydrochloride | 0.5635 |
| Sodium pyruvate | 385.0 |
| Thymidine | 2.555 |
| Alanine | 31.15 |
| Arginine, monohydrochloride | 780.5 |
| Asparagine, monohydrate | 589.435 |
| Aspartic acid | 465.05 |
| Cysteine, monohydrochloride, monohydrate | 122.92 |

TABLE 4-continued

| Component | Concentration (mg/l) |
| --- | --- |
| Cystine, dihydrochloride | 31.285 |
| Glutamic acid | 51.45 |
| Glutamine | 1606.0 |
| Glycine | 329.65 |
| Histidine, monohydrochloride, monohydrate | 94.36 |
| Isoleucine | 331.49 |
| Leucine | 491.55 |
| Lysine, monohydrochloride | 2007.05 |
| Methionine | 153.48 |
| Phenylalanine | 50.36 |
| Proline | 120.75 |
| Serine | 557.05 |
| Threonine | 749.95 |
| Tryptophan | 75.54 |
| Tyrosine, disodium salt, dihydrate | 194.025 |
| Valine | 439.55 |
| Biotin | 0.0256 |
| D-Calcium pantothenate | 3.68 |
| Choline chloride | 50.86 |
| Cyanocobalamin | 4.76 |
| Folic acid | 6.55 |
| i-Inositol | 66.60 |
| Nicotinamide | 2.1295 |
| Pyridoxal, monohydrochloride | 2.000 |
| Pyridoxine, monohydrochloride | 0.217 |
| Riboflavin | 0.3330 |
| Thiamine, monohydrochloride | 3.190 |
| Glucose | 4300.0 |
| Sodium bicarbonate | 1220.0 |
| Sodium chloride (to 350 mOsm) | 7360.0 |
| Pluronic F-68 Prill | 1000.0 |
| Gentamycin sulfate | 100.0 |

For some applications, the cell culture medium is desirably supplemented with glucose. Glucose is typically maintained at a minimum concentration of at least about 1.0 g/l, but may be as high as about 20 g/l. Satisfactory results may be obtained with a glucose concentration of about 10-15 g/l. The concentration of glucose may substantially decrease during culturing of the cells, depending on both the rate at which the cells utilize the glucose, and on the amount of time that the cells are cultured in the medium. Thus, it may be necessary to supplement the medium with added glucose to maintain at least the minimum required concentration during the culture period.

The cell culture medium may, for some preferred applications, have a folic acid level of from about 13.5 mg/l to about 35 mg/l.

While many mammalian cell culture media require a serum supplement such as fetal calf serum (FCS) or fetal bovine serum (FBS), the culture media used to practice this invention do not necessarily require a serum supplement. For large-scale culturing, such as in fermentors, serum is preferably omitted from the medium. However, serum is generally used for small-scale cell culturing. The preferred type of serum is FBS, and it is present at a concentration from about 0.1 to about 5 percent by volume, preferably from about 0.25 to about 2.5 percent, and most preferably from about 0.5 to about 1.0 percent.

In addition to srum, the media of this invention may contain various other supplements. One optional supplement is protein, termed "peptone", that has been hydrolyzed. The source of this protein may be animal by-products from slaughter houses, purified gelatin, or plant material. The protein is typically hydrolyzed using acid, heat or various proteases. Preferred peptone mixtures are "Primatone RL" and "Primatone HS", both of which are commercially available. Peptone, when used in the cell culture medium, is typically added to a final concentration of from about 0.1 to 5 percent, and preferably 0.1 to 1 percent, as calculated on a weight-to-volume basis.

Another supplement that may be used in this invention is HEPES (4-[2-Hydroxyethyl]-1-piperazine-ethanesulfonic acid) buffer orany other equivalent buffer. The buffer is preferably used for small-scale culturing of the cells at concentrations from about 5 to 25 mM, and preferably from about 10 to 15 mM. Large-scale cultures, as are grown in fermentors for example, will preferably not contain a buffer, since the fermentors typically use a pH-controlled buffering system.

Another supplement that is preferably present in the media of this invention is the hormone insulin. The optimal concentration of insulin may vary for each cell line cultured, and may be determined by routine methods not requiring undue experimentation. Some cell lines may be transfected, prior to culturing, with the insulin or proinsulin gene. Such cells are then capable of partially or entirely meeting their insulin needs through endogenous production of insulin. The amount of exogenous insulin added to these transfected cells will generally be lower than for comparable cells that have not been transfected with the proinsulin gene. Typically, cells transfected with the proinsulin gene may require exogenous insulin at concentrations from about 0.1 mg/l to about 10 mg/l, and preferably from about 0.1 mg/l to about 1 mg/l. Cells that have not been transfected with the proinsulin gene may require exogenous insulin at a concentration from about 1 mg/l to about 20 mg/l, and preferably from about 5 mg/l to about 10 mg/l.

The growth factor transferrin is another suitable supplement to the media of this invention. Generally, it is present at a concentration of from about 0.1 to 25 mg/l, preferably from about 5 to 25 mg/l, and most preferably from about 5-10 mg/l. Linoleic acid is also a preferred supplement in the media of this invention. Linoleic acid is typically commercially available in the form of a liquid stock that may contain vitamin E as well. The liquid stock is usually diluted into pure ethanol to a convenient concentration, and then added as a supplement to the culture media to a final concentration from about 1 $\mu$M to about 25 $\mu$M, preferably from about 1 $\mu$M to about 10 $\mu$M, and most preferably about 5 $\mu$M. It should be noted that many commercially available media powders contain linoleic acid in its solid form as a sodium salt. However, the liquid form, prepared as described above, is the preferable form as a media supplement.

Linoleic acid may also be added as a supplement in the form of a complex with BSA (bovine serum albumin). The BSA is preincubated with linoleic acid such that a complex is formed between the two compounds. This complex is then added to the medium and facilitates the uptake of the linoleic acid by the cells.

Crude extracts of lipids may also be used to supplement the media of this invention. The lipid extract may be obtained from any biological source, although one preferred source is plant material, and particularly soybeans (soybean lipid extract may be purchased from Avanti-Polar Lipd Inc., Telham, Alabama). Typically, the extract will contain from about twenty percent to about ninety-five percent lipid, the majority of which will be phospholipid. The extract may be added to the cell culture medium at a concentration of from about 1 $\mu$g per ml to about 200 $\mu$g per ml, preferably from about 1 μg per ml to about 100 μg per ml, and more preferably 1 μg per ml to about 50 μg per ml.

A variety of inorganic metal salts, commonly called trace elements, are also common supplements in the media of this invention. These trace elements are usually prepared as one very concentrated aqueous stock solution, preferably about 10,000 fold greater than the desired final concentration when added to the medium. During the preparation of this solution, concentrated hydrochloric acid, preferably about 6 N, is used as necessary (usually about up to 50 ml per liter of water) to acidify the solution such that the salts will dissolve. The typical salts that make up a suitable trace element solution are listed in Table 5 below. The concentrations listed are the preferred ranges for final concentrations in the culture medium. Certain cell lines may require some but not all of these trace elements for optimal growth. The concentrations listed may be modified as is necessary depending on the requirements of the particular cell line to be cultured in the medium. However, concentrations that are significantly above these levels may be toxic to the cells.

TABLE 5

| Component | Concentration (nmol/l) |
|---|---|
| Selenous acid | 75–100 |
| Manganese sulfate, tetrahydrate | 2–4 |
| Ammonium parmolybdate, tetrahydrate | 2–4 |
| Ammonium vanadium oxide | 13–17 |
| Nickel chloride, hexahydrate | 1–2 |
| Stannous chloride, dihydrate | 1–2 |
| Sodium metasilicate, nonahydrate | 1350–1650 |
| Zinc sulfate, heptahydrate | 6500–8500 |
| Ferrous sulfate, heptahydrate | 5500–6500 |
| Cupric sulfate, pentahydrate | 20–25 |

The preferred final concentration in the culture medium of each of the trace elements is as follows: selenous acid at 89.94 nmol/l; manganese sulfate tetrahydrate at 3.00 nmol/l; ammonium paramolybdate tetrahydrate at 2.99 nmol/l; ammonium vanadium oxide at 14.96 nmol/l; nickel chloride hexahydrate at 1.50 nmol/l; stannous chloride at 1.50 nmol/l; sodium metasilicate nonahydrate at 1498.84 nmol/l; zinc sulfate heptahydrate at 7516.52 nmol/l; ferrous sulfate heptahydrate at 6057.55 nmol/l; and cupric sulfate pentahydrate at 23.02 nmol/l.

Another group of commonly used supplements that are suitable for use in the media of this invention are antimicrobial and antibiotic substances, and other selective growth compounds. A variety of antimicrobial and antibiotic substances are available for use in culture media to inhibit or slow the growth of bacteria, yeasts, protozoa and other microbes. The concentration at which these compounds are effective will vary depending on the compound(s) used. However, the appropriate concentration range for each compound is normally specified in the instructions supplied with the compound when it is purchased.

The media of this invention are suitable for use as selective growth media by omitting and/or adding particular compounds that are used to facilitate the selection of cells that possess certain characteristics.

Selective growth media are often used to select for cells that either inherently possess a particular protein, or have been transformed with DNA encoding this protein and therefore express the protein. Typically, this protein will permit the cells to survive in either the presence of substances that are normally toxic, or in the absence of substances that are normally necessary for growth and survival. An example of such a selection system involves the protein dihydrofoltte reductase (DHFR). Cells containing DHFR do not require exogenous hypoxanthine, thymidine, or glycine for growth and survival, and thus these components are omitted from the medium when it is used to select for DHFR containing cells. However, cells that do not possess detectable levels of DHFR do require hypoxanthine, thymidine, and glycine for growth and survival.

III. PREPARATION OF MEDIA

The media of this invention are generally prepared by methods well known in the art. In a preferred method, the vessel to be used for preparation of the medium is first filled with purified water to a volume that is less than the desired volume that permits sufficient incorporation of solid and other ingredients. A convenient and satisfactory volume is about 80 percent of the final desired volume. Typically, the polymer Pluronic F-68 at a concentration of about 0.5 to 5 g/l, and preferably about 1 g/l is added to the water. Other similar polymers may be used as a substitute for, or in addition to, the Pluronic F-68. This polymer serves to act as a physical buffer against shear forces. The necessary amount of each of the solid ingredients in the medium is weighed out; these solid ingredients may be combined to form a mixture termed the "medium powder" or "basal medium powder". The solid ingredients included here are the amino acids, vitamins, glucose, and/or other carbohydrates, and inorganic salts such as calcium salts, copper salts, iron salts, potassium salts, sodium salts, magnesium salts, manganese salts, and zinc salts. Most commercially available medium powders are packaged with all ingredients present in the amount necessary to produce a final desired concentration when the powder is added to a specified volume of water.

The medium powder described above is added to the purified water/polymer solution, and the medium powder is dispersed in the water by mixing. To this solution is added the elevated amounts of the particular amino acids listed in Table 1 above, followed by sodium bicarbonate. Alternatively, as described above, the medium powder may be premixed with the elevated amounts of amino acids such that all solid ingredients are added to the purified water in one step.

The pH is then checked, and should be between 6.5 and 7.2. If necessary, it can be adjusted to approximately 7.0 using either 6 N HCl or NaOH crystals. An antibiotic, preferably Gentamycin sulfate in the range of about 50 to 1000 mg/l (milligrams per liter of medium), preferably about 50 to 500 mg/l, and most preferably about 100 mg/l, may then be added if deemed necessary. Other suitable antibiotics at appropriate concentrations are commonly used in addition to or as a substitute for Gentamycin. The medium is then brought to the final desired volume with purified water, and the pH is re-checked and adjusted, if necessary, to a final value of about 7.0. The next step in preparing the medium is to adjust the osmolarity (a measure of the total dissolved solids in the medium, measured as the number of osmoles of solute per liter of solution) to the proper level. This level may vary depending on the medium used, but in general it is in the range of about 275 to 400 mOsm (milliosmols), and usually about 300 to 350 mOsm. The osmolality (number of osmoles of solute per kilogram of water) may be conveniently measured using an osmometer, and, if necessary, may be adjusted with sodium chloride or other suitable salt.

The above steps constitute preparation of the medium containing the elevated levels of amino acids. This medium may be further supplemented with other components, preferably added in the order listed as follows.

If serum is to be used in the medium, it is preferably added at this point. The BSA/lipid mixture may also be added at this point. The medium is preferably filtered through a sterilizing filter (0.22 micron mesh or less) before adding subsequent components. After filtration, additional supplements including, for example, trace elements (which preferably is prepared as a stock solution as discussed above), insulin, transferrin, and linoleic acid, are added. The amount of each of these supplements that is added to the medium will be predetermined, as discussed above.

IV. USE OF THE MEDIA

The media of this invention are particularly useful for culturing cells at high densities (at least 100,000 cells per milliliter of medium, and often 600,000 or 1,000,000 cells per milliliter of medium). In addition, culturing cells in these media typically results in an enhanced yield of product as compared with culturing the cells in publicly available media.

The completed medium may be used for culturing a variety of mammalian cells. The medium is inoculated with the selected host cells. Preferably, the inoculum volume will be on the order of about one-fifth of the volume of the medium, although some variation from this inoculum volume is acceptable. After inoculation, the culture is maintained in an appropriate environment (with respect to temperature, light, and carbon dioxide concentration).

The media of this invention may be used for culturing the cells as a monolayer or, preferably, for culturing the cells in suspension. The cells may be grown as a small-scale culture, i.e. in volumes of about 2 liters or less. Alternatively, and preferably, the cells are cultured in large volumes such as up to about 16 liters in spinner flasks or about 80 liters or more in fermentors designed for commercial production of biological compounds from animal cells. The cells are preferably grown as either small-scale suspension cultures or large-scale suspension cultures at a density of at least 100,000 cells per milliliter, which is considered to be a high density culture.

The cells themselves or a biological compound inside of the cells may be the desired end-product of the culturing. If so, they may be harvested and separated from the culture medium. Alternatively, a protein or other organic compound secreted by the cells into the medium may be the desired end-product of the culturing. In this situation, the medium may be separated from the cells, and the compound of interest can then be purified from the medium.

The following examples illustrate a preferred mode for practicing the invention, but should not be construed to limit the invention. All literature citations herein are expressly incorporated by reference.

EXAMPLES

Example 1

Chinese hamster ovary cells (CHO-K1, ATCC CCl 61) were transfected with the cDNA encoding human tissue plasminogen activator (t-PA). The transformed cells were amplified for t-PA production, and then placed in suspension in either control medium (1:1 Ham's F12:DMEM, both purchased from Gibco Laboratories, Grand Island, NY and prepared according to manufacturer's instructions) or Super medium, the composition of which is provided in Table A below. The cells were added to each medium at a density of between 600,000 and 800,000 cells/ml. Four ml aliquots of cell suspension in Super medium were added to each of 3 60 mm petri plates. Three other petri plates each received a four ml aliqout of cell suspension in control medium. Each plate was supplemented with 1 mg/l transferrin, 1.4 mg/l linoleic acid/ethanol, 2-5 mg/l bovine insulin, and the following trace elements, prepared as a stock solution as described above for Table 5. The trace element solution contained (at final concentrations after addition to the medium) selenous acid at 89.94 nmol/l; manganese sulfate tetrahydrate at 3.00 nmol/1: ammonium paramolybdate tetrahydrate at 2.99 nmol/1: ammonium vanadium oxide at 14.96 nmol/l; nickel chloride hexahydrate at 1.50 nmol/l; stannous chloride at 1.50 nmol/l; sodium metasilicate nonahydrate at 1498.84 nmol/l; zinc sulfate heptahydrate at 7516.52 nmol/l; ferrous sulfate heptahydrate at 6057.55 nmol/l; and cupric sulfate pentahydrate at 23.02 nmol/l.

The petri plates were then placed in an incubator at 37° C. and 5% $CO_2$, and maintained for 8 days.

TABLE A

| Component | Concentration (mg/l) |
|---|---|
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Hypoxanthine | 16.695 |
| Linoleic acid | 0.294 |
| Lipoic acid | 0.735 |
| Putrescine, dihydrochloride | 0.5635 |
| Sodium pyruvate | 385.0 |
| Thymidine | 2.555 |
| Alanine | 31.15 |
| Arginine, monohydrochloride | 780.5 |
| Asparagine, monohydrate | 589.435 |
| Aspartic acid | 465.05 |
| Cysteine, monohydrochloride, monohydrate | 122.92 |
| Cystine, dihydrochloride | 31.285 |
| Glutamic acid | 51.45 |
| Glutamine | 1606.0 |
| Glycine | 329.65 |
| Histidine, monohydrochloride, monohydrate | 94.36 |
| Isoleucine | 331.49 |
| Leucine | 491.55 |
| Lysine, monohydrochloride | 2007.05 |
| Methionine | 153.48 |
| Phenylalanine | 50.36 |
| Proline | 120.75 |
| Serine | 557.05 |
| Threonine | 749.95 |
| Tryptophan | 75.54 |
| Tyrosine, disodium salt, dihydrate | 194.025 |
| Valine | 439.55 |
| Biotin | 0.0256 |
| D-Calcium pantothenate | 3.68 |
| Choline chloride | 50.86 |
| Cyanocobalamin | 4.76 |
| Folic acid | 6.55 |
| i-Inositol | 66.60 |
| Nicotinamide | 2.1295 |
| Pyridoxal, monohydrochloride | 2.000 |
| Pyridoxine, monohydrochloride | 0.217 |
| Riboflavin | 0.3330 |
| Thiamine, monohydrochloride | 3.190 |

TABLE A-continued

| Component | Concentration (mg/l) |
| --- | --- |
| Glucose | 4300.0 |
| Sodium bicarbonate | 1220.0 |
| Sodium chloride (to 350 mOsm) | 7360.0 |
| Pluronic F-68 Prill | 1000.0 |
| Gentamycin sulfate | 100.0 |

After four days in culture, an additional 4 g/l of glucose was added to each plate to give an approximate concentration of 9 g/l of glucose for the entire duration of culturing.

At six days of culturing, a 50 µl aliqout of culture fluid was removed from each plate. The amount of t-PA present in this medium was then assayed and quantitated using standard enzyme-linked immunosorbent assay (ELISA) with a monoclonal antibody directed to t-PA. This process was repeated on days seven and eight of culturing.

Figure 1:
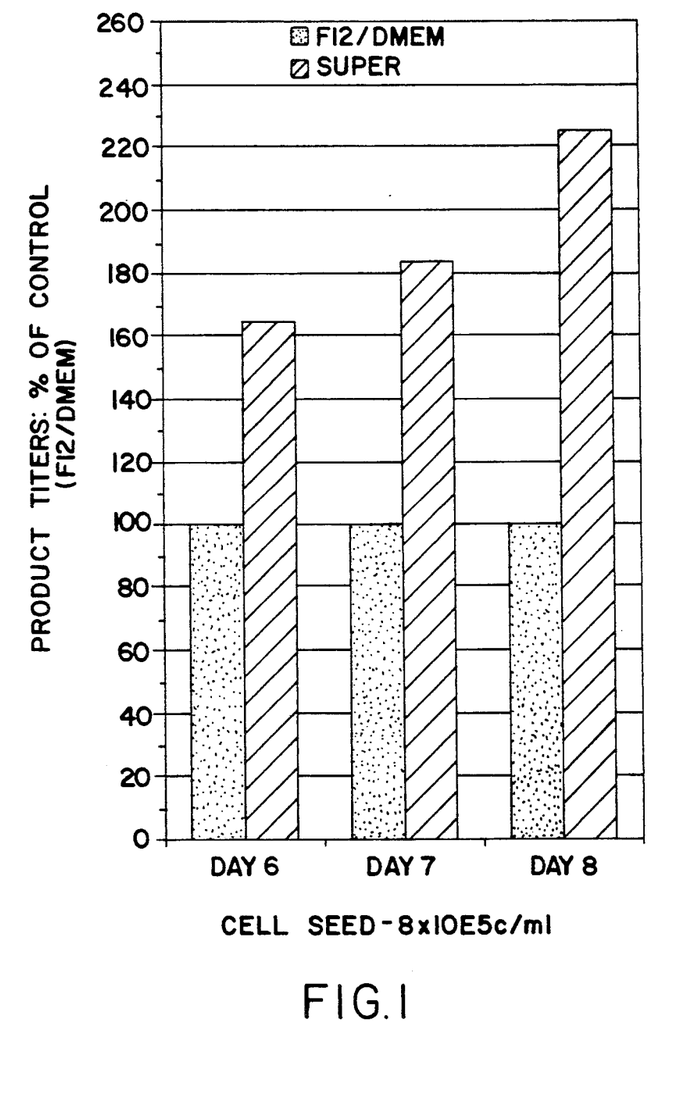
FIG. 1 depicts the relative amount of recombinant tissue plasminogen activator (rt-PA) produced and secreted into the culture medium by a clonal cell strain of Chinese hamster ovary (CHO) cells transfected with the DNA encoding t-PA, and grown in either control (solid black) or Super (hatched lines) medium. Assays for t-PA levels were conducted after 6, 7, and 8 days of culturing.

The results are shown in FIG. 1. Each bar is an average of the data obtained from three petri plates. At six days of culturing, the culture fluid obtained from cells grown in Super had sixty percent more t-PA as compared to the culture fluid obtained from cells grown in the control medium. At seven days of culturing, the Super culture fluid had eighty percent more t-PA, and at eight days the Super medium had over one hundred percent more t-PA than the control culture fluid.

Example 2

Chinese hamster ovary cells (CHO-K1, ATCC CCl 61) were transfected with the cDNA encoding DNase. The transformed cells were amplified for DNase production, and then placed in suspension in either control medium (1:1 Ham's F12:DMEM, both purchased from Gibco Laboratories, Grand Island, NY and prepared according to manufacturer's instructions) or Super medium, the composition of which is provided in Table A above. The cells were added to each medium at a density of between 600,000 and 800,000 cells/ml. Four ml aliqout of cell suspension in Super medium were added to each of three 60 mm petri plates. Three other petri plates each received a four ml aliqout of cell suspension in control medium. Each plate was supplemented with 1 mg/l transferrin, 1.4 mg/l linoleic acid/ethanol, 2–5 mg/l bovine insulin, and the following trace elements, prepared as a stock solution as described above for Table 5. The trace element solution contained (at final concentrations after addition to the medium) selenous acid at 89.94 nmol/l; manganese sulfate tetrahydrate at 3.00 nmol/l; ammonium paramolybdate tetrahydrate at 2.99 nmol/l; ammonium vanadium oxide at 14.96 nmol/l; nickel chloride hexahydrate at 1.50 nmol/l; stannous chloride at 1.50 nmol/l; sodium metasilicate nonahydrate at 1498.84 nmol/l; zinc sulfate heptahydrate at 7516.52 nmol/l; ferrous sulfate heptahydrate at 6057.55 nmol/l; and cupric sulfate pentahydrate at 23.0 nmol/l.

The petri plates were then placed in an incubator at 37° C. and 5% CO2, and maintained for 8 days.

After four days in culture, an additional 4 g/l of glucose was added to each plate to give an approximate concentration of 9 g/l of glucose for the entire duration of culturing.

At six days of culturing, a 50 µl aliqout of culture fluid was removed from each plate. The amount of DNase present in this medium was then assayed and quantitated using standard enzyme-linked immunosorbent assay (ELISA) with a monoclonal antibody directed to DNase. This process was repeated on days seven and eight of culturing.

Figure 2:
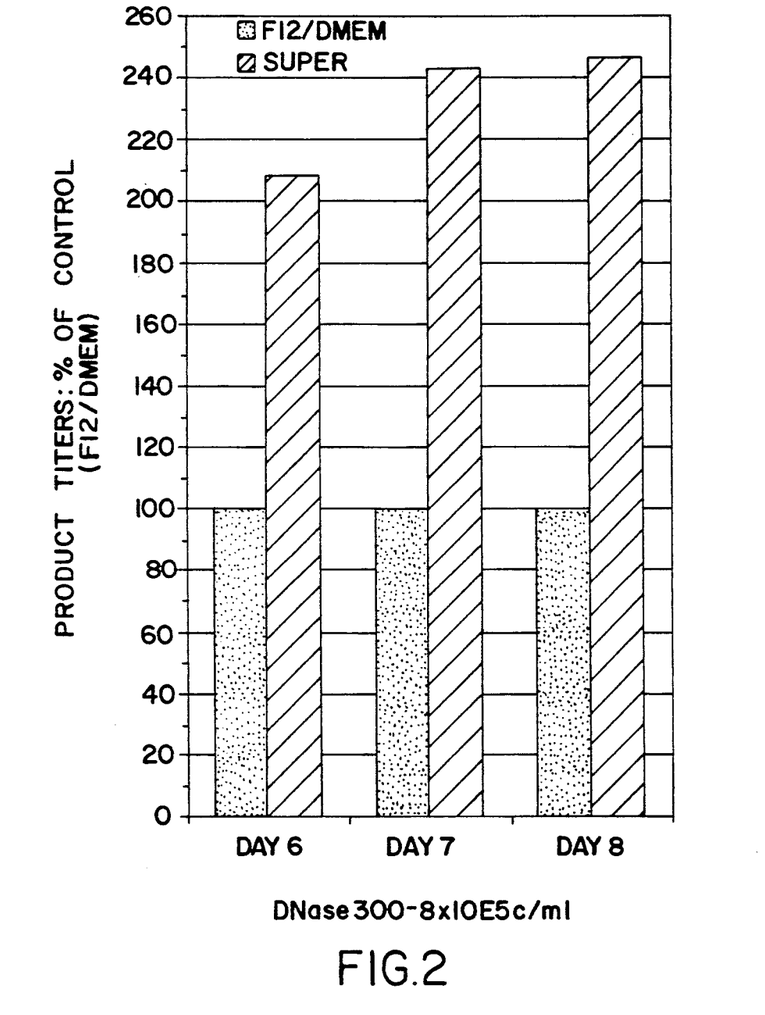
FIG. 2 depicts the relative amount of DNase produced and secreted into the culture medium by a clonal cell strain of Chinese hamster ovary (CHO) cells grown in either control (solid black) or Super (hatched lines) medium. Assays for DNase levels were conducted after 6, 7, and 8 days of culturing.

The results are shown in FIG. 2. The data is the average obtained from the three petri plates. At six days of culturing, the culture fluid obtained from cells grown in Super had more than twice as much DNase as compared to the culture fluid obtained from cells grown in the control medium. At seven days of culturing, the Super culture fluid had one hundred and forty percent more, and this level was maintained at eight days of culturing.

We claim:

1. A method for culturing Chinese hamster ovary cells to improve production of recombinant proteins produced by said cells comprising culturing the cells in a culture medium containing the following components: asparagine at a concentration of from about 300 mg/l to about 750 mg/l, aspartic acid at a concentration of from about 300 mg/l to about 650 mg/l, glycine at a concentration of from about 300 mg/l to about 500 mg/l, isoleucine at a concentration of from about 300 mg/l to about 500 mg/l, leucine at a concentration of from about 400 mg/l to about 700 mg/l, lysine at a concentration of from about 1000 mg/l to about 2250 mg/l, methionine at a concentration of from about 80 mg/l to about 350 mg/l, serine at a concentration of from about 500 mg/l to about 750 mg/l, threonine at a concentration of from about 550 mg/l to about 950 mg/l, tryptophan at a concentration of from about 75 mg/l to about 230 mg/l, tyrosine at a concentration of from about 175 mg/l to about 400 mg/l, and valine at a concentration of from about 240 mg/l to about 640 mg/l.

2. The method of claim 1 wherein the culture medium further contains folic acid at a concentration of from about 13.5 mg/l to about 35 mg/l.

3. A method for culturing Chinese hamster ovary cells to improve production of recombinant proteins produced by said cells comprising culturing the cells in the following culture medium consisting essentially of the following components at the indicated concentrations:

| Component | Concentration (mg/l) |
| --- | --- |
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Linoleic acid | 0.294 |
| Lipoic acid | 0.735 |
| Putrescine, dihydrochloride | 0.5635 |
| Sodium pyruvate | 385.0 |
| Alanine | 31.15 |
| Arginine, monohydrochloride | 780.5 |
| Asparagine, monohydrate | 300–750 |
| Aspartic acid | 300–650 |
| Cysteine, monohydrochloride, monohydrate | 122.92 |
| Cystine, dihydrochloride | 31.285 |
| Glutamic acid | 51.45 |
| Glutamine | 1606.0 |
| Glycine | 300–500 |
| Histidine, monohydrochloride, monohydrate | 94.36 |
| Isoleucine | 300–500 |

-continued

| Component | Concentration (mg/l) |
|---|---|
| Leucine | 400–700 |
| Lysine, monohydrochloride | 1000–2250 |
| Methionine | 80–350 |
| Phenylalanine | 50.36 |
| Proline | 120.75 |
| Serine | 500–750 |
| Threonine | 500–950 |
| Tryptophan | 75–230 |
| Tyrosine, disodium salt, dihydrate | 175–400 |
| Valine | 250–640 |
| Biotin | 0.0256 |
| D-Calcium pantothenate | 3.68 |
| Choline chloride | 50.86 |
| Cyanocobalamin | 4.76 |
| Folic acid | 13.5–35 |
| i-Inositol | 66.60 |

-continued

| Component | Concentration (mg/l) |
|---|---|
| Nicotinamide | 2.1295 |
| Pyridoxal, monohydrochloride | 2.000 |
| Pyridoxine, monohydrochloride | 0.217 |
| Riboflavin | 0.3330 |
| Thiamine, monohydrochloride | 3.190 |
| Glucose | 4300.0 |
| Sodium bicarbonate | 1220.0 |
| Sodium chloride (350 mOsm) | 7360.0 |
| Pluronic F-68 Prill | 1000.0 |
| Gentamycin sulfate | 100.0 |

4. The method of claim 3 wherein the cells are grown and maintained at a density of at least 100,000 cells per ml of culture medium.

5. The method of claim 3 wherein the cell culture medium further contains hypoxanthine at a concentration of about 16.695 mg/l and thymidine at a concentration of about 2.55 mg/l.

* * * * *